United States Patent [19]

Reynolds

[11] Patent Number: 4,886,495
[45] Date of Patent: Dec. 12, 1989

[54] VIAL-BASED PREFILLED SYRINGE SYSTEM FOR ONE OR TWO COMPONENT MEDICAMENTS

[75] Inventor: David L. Reynolds, Montreal, Canada

[73] Assignee: Duoject Medical Systems Inc., Montreal, Canada

[21] Appl. No.: 72,015

[22] Filed: Jul. 8, 1987

[51] Int. Cl.$^4$ ............................................. A61M 5/00
[52] U.S. Cl. ..................... 604/88; 604/191; 604/416; 604/413; 206/222
[58] Field of Search .................... 604/82, 87, 88, 89, 604/91, 92, 191, 200, 201, 203–205, 411, 413–416, 905; 206/222; 215/247

[56] References Cited

U.S. PATENT DOCUMENTS

| | | | |
|---|---|---|---|
| 1,279,530 | 9/1918 | Fitting | 604/192 |
| 2,684,068 | 7/1954 | Orens | 604/88 |
| 2,842,126 | 7/1958 | Brown | 604/243 |
| 3,150,661 | 9/1964 | Maki | 604/243 |
| 3,437,090 | 4/1969 | Sarnoff . | |
| 3,477,432 | 11/1969 | Shaw . | |
| 3,489,147 | 1/1970 | Shaw . | |
| 3,542,240 | 11/1970 | Solowey | 604/415 |
| 3,547,122 | 12/1970 | Rinser | 604/88 |
| 3,563,373 | 2/1971 | Paulson | 604/88 |
| 3,570,486 | 3/1971 | Engelsher | 604/88 |
| 3,636,950 | 1/1972 | Gomez et al. | 604/88 |
| 3,659,749 | 5/1972 | Schwartz | 222/145 |
| 3,678,931 | 7/1972 | Cohen . | |
| 3,682,174 | 8/1972 | Cohen . | |
| 3,685,514 | 8/1972 | Cheney . | |
| 3,724,460 | 4/1973 | Gomez et al. | 604/88 |
| 3,785,379 | 1/1976 | Cohen . | |
| 3,845,763 | 11/1974 | Cloyd . | |
| 3,872,867 | 3/1975 | Killinger | 604/413 |
| 3,923,059 | 12/1975 | Ogle | 604/231 |
| 3,994,296 | 11/1976 | Cloyd | 604/203 |
| 4,014,330 | 3/1977 | Genese | 604/88 |
| 4,055,177 | 10/1977 | Cohen . | |
| 4,059,109 | 11/1977 | Tischlinger . | |
| 4,060,082 | 11/1977 | Lindberg et al. . | |
| 4,072,149 | 2/1978 | Tischlinger . | |
| 4,116,240 | 9/1978 | Guiney . | |
| 4,171,698 | 10/1979 | Genese | 604/88 |
| 4,180,070 | 12/1979 | Genese | 604/88 |
| 4,313,440 | 2/1982 | Ashley . | |
| 4,405,317 | 9/1983 | Case | 604/90 |
| 4,424,057 | 1/1984 | House | 604/88 |
| 4,445,895 | 5/1984 | Margulies | 604/193 |
| 4,464,174 | 8/1984 | Ennis | 604/90 |
| 4,581,016 | 4/1986 | Gettig | 604/92 |
| 4,581,023 | 4/1986 | Kuntz | 604/234 |
| 4,755,169 | 7/1988 | Sarnoff et al. | 604/191 |

FOREIGN PATENT DOCUMENTS

| | | |
|---|---|---|
| 1766151 | 6/1971 | Fed. Rep. of Germany . |
| 724671 | 2/1955 | United Kingdom . |
| 1030861 | 5/1966 | United Kingdom . |
| 1122787 | 8/1968 | United Kingdom . |
| 1252306 | 11/1971 | United Kingdom . |
| 1444119 | 7/1976 | United Kingdom . |
| 1525455 | 9/1978 | United Kingdom . |

Primary Examiner—Stephen C. Pellegrino
Assistant Examiner—Ralph Lewis
Attorney, Agent, or Firm—Ridout & Maybee

[57] ABSTRACT

A prefilled syringe for one or two component medicaments is based upon the use of a vial containing a medicament or one component of a medicament, the vial having an open bottom closed by a piston. When the piston is coupled with a plunger, and an adapter cap having an internal needle and an external connection for a needle is placed over a cap of the vial, the latter is converted into a prefilled syringe. The piston has an axial passage closed by a resealable septum, so that a separate diluent stored in a flexible capsule may be introduced into the vial through the piston by a double ended needle mounted on a further cap applied to the capsule, the further cap being coupled within the tubular interior of the plunger so that the double ended needle penetrates the septum in the piston. The capsule is pushed forward onto the double ended needle when its contents are to be expelled into the vial. The capsule and its cap are then removed and discarded.

13 Claims, 3 Drawing Sheets

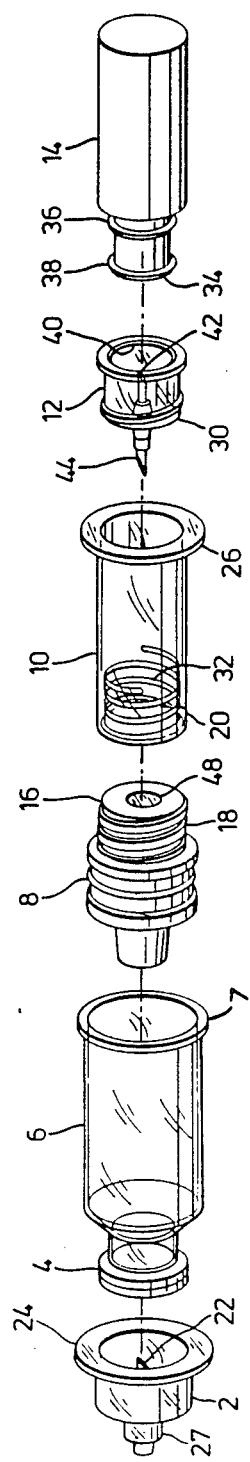
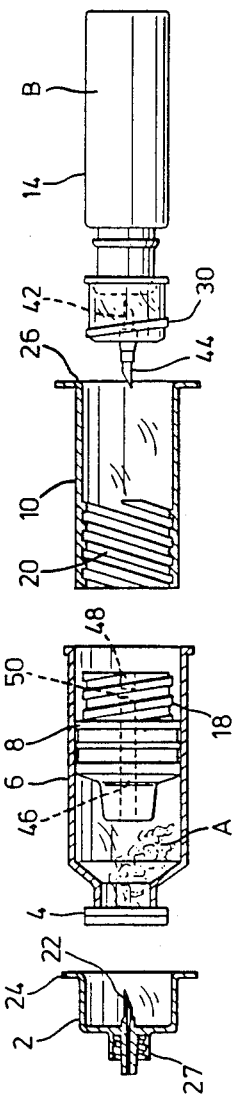
FIG. 1
FIG. 2

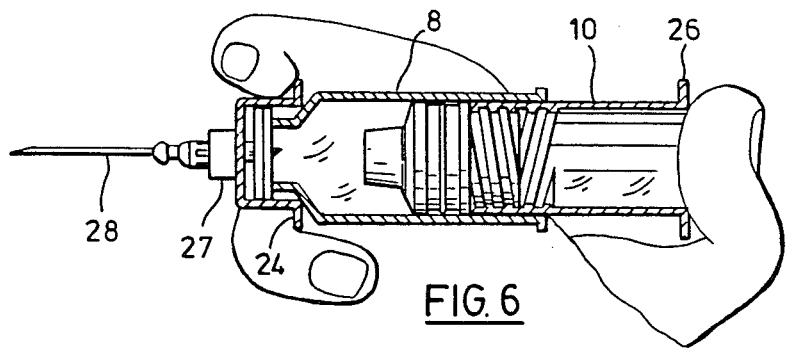
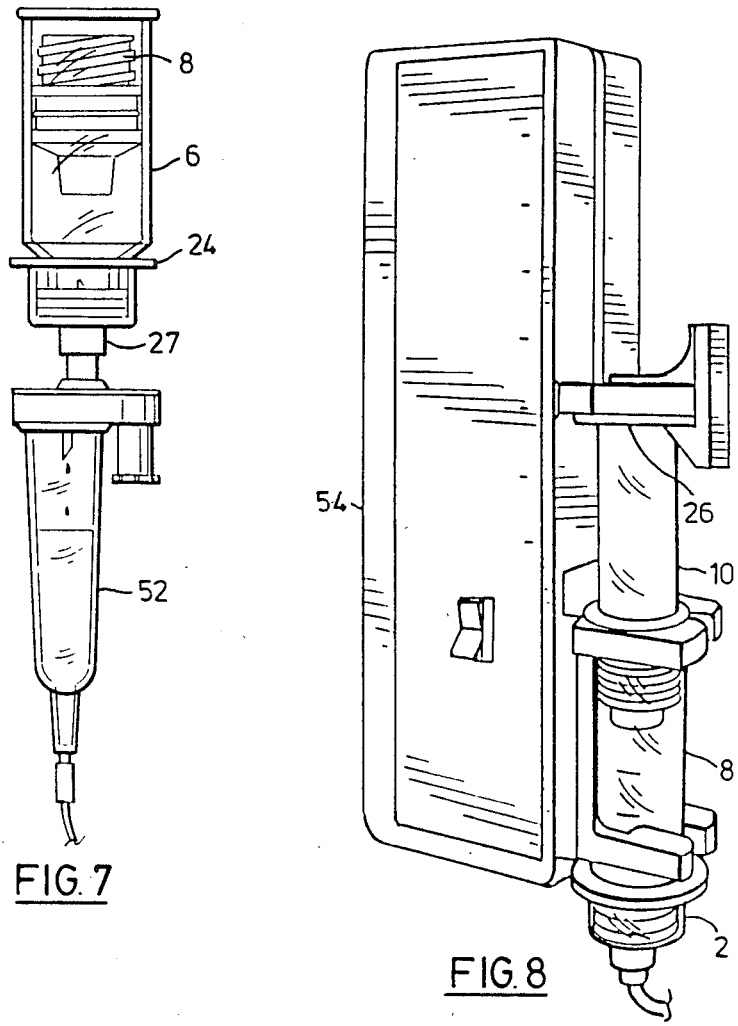

VIAL-BASED PREFILLED SYRINGE SYSTEM FOR ONE OR TWO COMPONENT MEDICAMENTS

FIELD OF THE INVENTION

This invention relates to prefilled syringes for use in medical or veterinary treatment.

BACKGROUND OF THE INVENTION

There has been an increasing trend in recent years to the putting up of pharmaceuticals in dosage forms so as to minimize the preparation required to administer a medicament to a patient and to reduce the chances of dosage errors or contamination. One dosage form which has been gaining rapid acceptance is the prefilled disposable syringe. Various difficulties are however associated with the preparation and usage of such syringes, particularly in the case of preparations which, in ready to use condition, have a short shelf life. Numerous forms of dual compartment syringe structure have been proposed for the shipping of such preparations with components stored in separate compartments for admixture immediately prior to use. Although certain structures have met with some degree of acceptance, they are commonly difficult to manufacture and/or use because of difficulties in filling the syringe with the components, and because they require extensive manipulation immediately prior to use. Moreover, they are frequently substantially more bulky than conventional syringes because in many cases they frequently comprise components which effectively represent two syringes in tandem. Prior art in this field is discussed in my copending U.S. patent application No. 018,934, filed Feb. 25, 1987 as a continuation in part of my application No. 759,432 filed July 26, 1985 and now abandoned.

Problems in the manufacture of prefilled syringes are not confined to two component systems and even with single component systems the filling of syringes under factory conditions is difficult to mechanize effectively and requires special filling machinery. The same applies to related units prefilled with liquids required for injection or infusion during medical procedures.

SUMMARY OF THE INVENTION

The present invention seeks to provide a system for the distribution of preparations required for injection or infusion in liquid dosage form during medical procedures, which has a wide range of utility both for single component liquid preparations or for two component systems of which one component may be a solid, which utilizes a small number of components all suitable for mass production, and which is simple to assemble and fill utilizing available equipment.

The system comprises a sequence of components of which various subsequences can be combined to form injection systems for preparations requiring shipment and storage as two separate components, certain subsequences themselves having utility respectively as injection systems for single component liquid preparations. "Injection" is utilized broadly to cover hypodermic, intramuscular and intravenous injection, gravity and mechanical infusion, and injection into other vessels utilized in medical treatment or testing. For the purposes of description, the "front" of an injection system will be considered the end of the system from which a liquid preparation is so injected.

In its form as an assembled system for the dispensing of preparations stored as two components, the system comprises, in sequence from front to rear, a rearwardly facing outer cap having a forwardly facing attachment for engagement with a hollow needle or other dispensing instrumentality and a rearwardly facing hollow piercing needle within and of a depth less than the cap; a rearwardly facing inner cap which is capped by the outer cap, the latter including means by which it may be forced rearwardly relative to the inner cap so that the inwardly facing piercing needle of the outer cap penetrates the inner cap; a generally cylindrical vial closed at its front end by said inner cap and open at its rear end; a first component of the preparation within the vial; a piston axially movable within the vial and maintaining said first component sealed within said vial between the inner cap and the piston; a hollow cylindrical plunger to the rear of the piston, the piston and plunger having coupling means enabling the plunger to be manipulated from a relatively rearward position relative to the piston to a relatively forward position relative to the piston; a third cap received within and releasably engageable with the interior of a forward end of the plunger, the third cap having a double ended hollow needle having both forward and rearward projections, the forward projection of the needle being such that when the third cap is engaged with the plunger, and the plunger is in its rearward position relative to the piston, the needle does not penetrate the plunger, and the plunger is in its forward position relative to the piston, the needle does penetrate the plunger; and a sealed collapsible capsule containing a second, liquid component of the preparation, the capsule having a front portion for entering the rear end of the plunger and engaging with the third cap, and a deformable rear portion extending rearwardly of the plunger whereby the rear portion may be manipulated to drive the forward portion of the capsule onto the rearward projection of the needle and permit the contents of the capsule to be discharged through the needle.

The above arrangement has a number of advantages in the manufacture and use of prefilled syringes for two component systems; furthermore, without the third cap and the sealed capsule containing the second component the remaining components provide, according to a further feature of the invention, advantages in the manufacture and use of prefilled syringes for single component systems. The third cap and sealed capsule provide, according to yet a further feature of the invention, an advantageous subsystem for various applications in which a sealed sterile source of a liquid is required for injection, or dropwise introduction into other containers used in medical procedures. With prefilled syringes for two component systems, either the capsule or the capsule and the third cap, may be sold, or shipped separately. This enables different diluents or sizes of capsule to be selected, or a common set of diluent capsules to be utilized with syringe assemblies containing different first components, thus simplifying inventory control.

The first component may be introduced into the vial through its front end, after insertion of the piston in its rear end, using conventional vial filling equipment to introduce the first component and apply the inner cap. The invention also extends to such a vial containing material intended for injection, which may be converted to a syringe by the addition of components as described above. The capsules may similarly be prepared utilizing known capsule filling equipment.

Further features of the invention will become apparent from the following description of a preferred embodiment thereof with reference to the accompanying drawings.

BRIEF DESCRIPTION OF THE DRAWINGS

In the drawings:

FIG. 1 is a perspective exploded view of the mechanical components of a syringe system in accordance with the invention;

FIG. 2 is a partially longitudinally sectioned, partially exploded view of the syringe components showing some further details of their construction;

FIGS. 6, 7 and 8 illustrate exemplary applications of the syringe.

DESCRIPTION OF THE PREFERRED EMBODIMENTS

Figure 3:
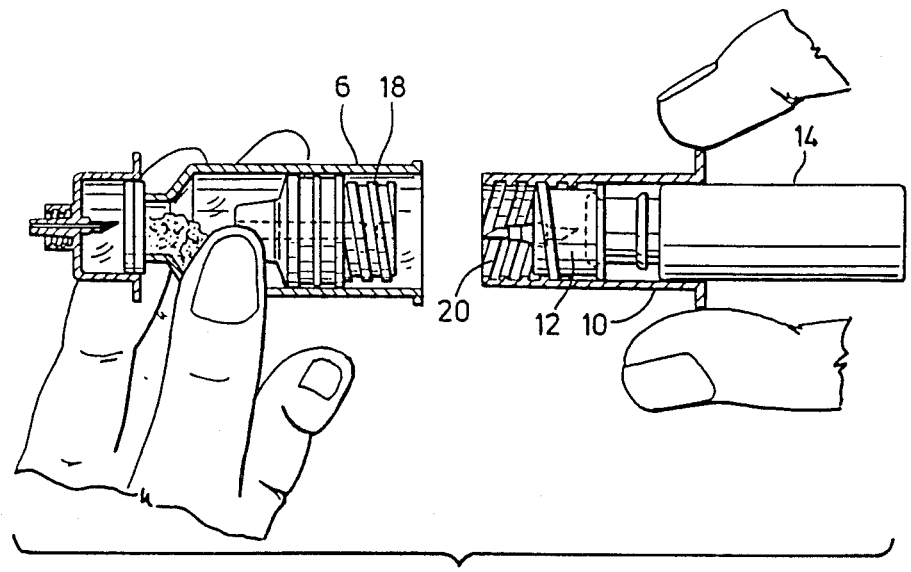
FIGS. 3, 4 and 5 illustrate preparation of the syringe system to provide a syringe ready for use.

Referring to FIGS. 1 and 2, a syringe system for the injection of a liquid preparation stored as two components comprises seven primary mechanical components, apart from the components of the preparation, which latter are shown in FIG. 2 but not FIG. 1. The components of the preparation typically comprise a first component A which may be in any physical state suitable for storage in a vial, and a second liquid component B, typically but not necessarily sterile water. The liquid component B is stored in a sealed capsule 14 of flexible material, manufactured using conventional techniques from a material, usually synthetic plastic, which is compatible with the contents of the capsule. The first component is stored in a cylindrical vial 6, typically of glass, and capped by a cap 4, utilizing conventional vial filling and capping equipment. A front end of the vial 6, shown in more detail in FIG. 9, capped by the cap 4, has a relatively large opening characteristic of such vessels, so that filling with either liquids or solids can be readily achieved. The cap 4 is cylindrical, and formed by an aluminum sleeve 4a, having an inwardly extending flange 4b retaining a soft rubber disc 5 over the front end opening 5a of the vial, so as to define a conventional needle penetrable central zone. The cap is tightly crimped onto a flange 5b of the neck at the front end of the vial so as to seal the latter. A major difference from conventional vials is that the conventional bottom wall of the vial is replaced by an axially movable piston 8 in sealing contact with the vial walls. When received within the vial 6, this piston in no way interferes with the handling of the vial using conventional machinery, and in particular permits the vial to be stood on its rear end with its front end upwards as it passes through a filling machine.

The filled vial 6 may be converted into a pre-filled syringe by applying an outer cap 2 over the cap 4 and attaching a cylindrical plunger sleeve 10 to the piston 8. The piston 8, typically formed of rubber, is moulded with a rearward extension 16 with an external thread 18, while the interior of the front end of the plunger sleeve 10 is formed with a complementary internal thread 20 so that it may be screwed onto the piston 8. The outer cap 2 fits over the inner cap 4 so that a hollow needle 22 formed within the cap 2 does not reach the penetrable zone of the cap 4. On the front of the cap 2 and in communication with the hollow needle 2 is a coupling adapter 27 for example similar to those sold under the trade mark LUER-LOK, for connection of the syringe to a needle 28 or other instrumentality (see FIGS. 6–8). The rear ends of both cap 2 and the sleeve 10 are formed with radially extending flanges 24 and 26 respectively which form finger grips for operation of the syringe. Thus if a user grips the syringe by the flanges as shown in FIG. 6 and presses them towards each other, the cap 2 is pulled rearwardly onto the cap 4 so that the needle 22 penetrates the cap and the contents of the syringe can be expelled through the needle 22 and the needle 28. It will be noted that the rear end of the vial 6 is formed with only a relatively slight external flange 7 rather than the wide finger flange commonly found on the barrels of conventional syringes. In the present arrangement, the flange 24 provides the function of such a finger flange, enabling the flange 7 to be reduced to a size which will avoid such interference between the flanges of adjacent vials as would cause tipping when the vials are conveyed in a vertical attitude through filling and capping equipment.

A prefilled syringe so constructed has significant advantages over conventional prefilled syringe in that the vial may be filled using conventional vial filling equipment, and yet may be utilized directly instead of requiring its contents to be transferred to a syringe prior to use as has been conventional in the use of vials.

The vial may also be charged with material which is not directly injectable, such as solids which must be dissolved or suspended in a liquid medium prior to injection. In this case the liquid medium is sealed as already described in a flexible capsule 14. A third cap 12 is either applied to the capsule as shown in FIG. 2, or inserted into the plunger sleeve 10 so that a screw thread 30 on the exterior of the cap engages the screw thread 20 within the sleeve.

Figure 9:
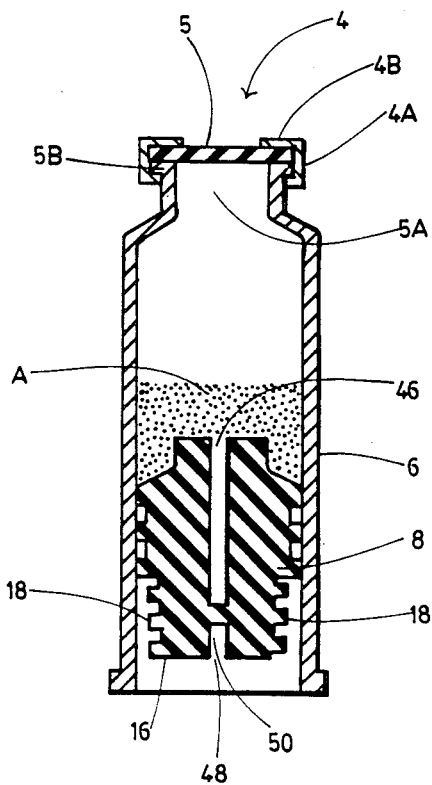
FIG. 9 is a longitudinal section on an enlarged scale of a vial used in the syringe system.

A neck 34 of the capsule 14 has two peripheral ridges 36 and 38. If the cap 12 is applied to the capsule, a detent 40 within the cap is pushed over only the outer ridge 38 so that a rear end portion 42 of a hollow needle mounted in the cap stops short of the end of the capsule. By forcing the detent 40 rearwardly over the ridge 36, the needle portion 42 can be forced rearwardly so as to penetrate the capsule. A forward end portion 44 of the hollow needle has a length such that when the cap 12 is screwed into the sleeve 10, and the sleeve 10 is screwed onto the piston 8, the needle portion 44 penetrates a resilient septum 50 normally separating axial passages 46 and 48 formed in the front and rear of the piston as best seen in FIG. 9.

Figure 4:
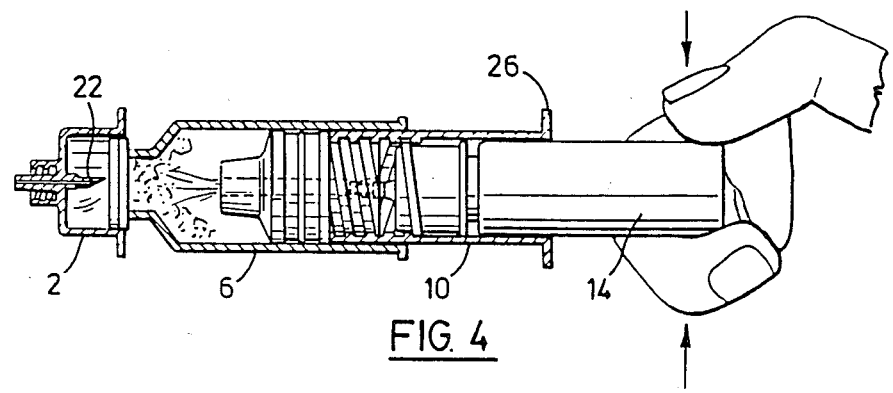
Figure 5:
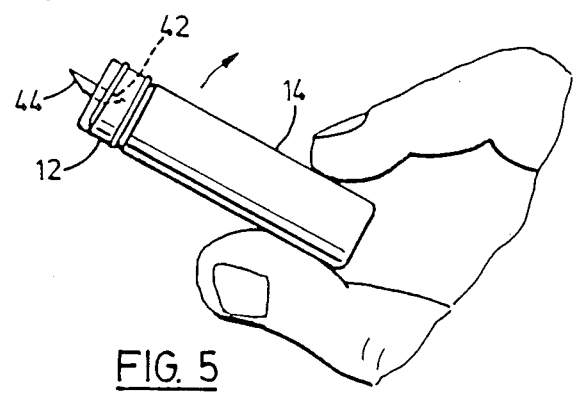

In use, if the capsule 14 and cap 12 are shipped as a separate unit, this unit is screwed into the sleeve 10 (see FIG. 3), and the sleeve 10 is pushed into the rear of the vial 6 so that the needle portion 44 penetrates the septum 50 of the piston 8 and the thread 20 is screwed onto the thread 18 of the piston (see FIG. 4). This action also substantially unscrews the cap 12 from the thread 20. The capsule 14 is then pressed forward onto the needle portion 42, and the liquid contents of the capsule can then be squeezed through the needle and into admixture with the first component in front of the piston 8. Thereafter the capsule 14 and cap 12 may be pulled as a unit from the sleeve 10 and discarded (see FIG. 5). The septum 50 reseals as the needle portion 44 is withdrawn, leaving a syringe ready for use as illustrated in FIGS. 6–8. Alternatively, if the cap 12 is prefitted to the sleeve, the sleeve 10 may be screwed onto the piston 8, and the capsule 14 pressed into the sleeve 10 and the cap so as to establish communication between the capsule and the space forward of the piston, the procedure thereafter being the same.

Rather than being used conventionally with a needle as shown in FIG. 6, the prepared syringe may be used for gravitational or mechanical infusion as shown in FIGS. 7 and 8. In FIG. 7, the adapter 27 is fitted to a complementary coupling on a gravity infuser 52 to provide a drip feed, the sleeve 10 having been unscrewed and discarded, together with the cap 12 and capsule 14, if used. In FIG. 8, the syringe is mounted in a mechanical infuser 54 such as that sold under the trade mark BARD, the latter being equipped with clamps 56, 58, 60 suited for engagement with the syringe.

By basing the system on an open-bottomed vial 6 closed at its bottom end by a piston 8 equipped with means such as the screw thread 18 for coupling it to a plunger of sleeve form, and with a needle penetrable septum 50, in optional conjunction with sealed flexible capsules of diluent, great flexibility in application can be obtained, using components which are easy to fill, compact to ship, and easy to make ready for use.

I claim:

1. A syringe system comprising, in sequence of assembly from front to rear:
   (a) an outer cap defining a hollow interior facing rearwardly, the cap having a forwardly facing attachment for engagement with a hollow needle or other dispensing instrumentality and a rearwardly facing hollow piercing needle within the hollow interior of the cap;
   (b) a rearwardly facing annular inner cap which contains an elastomeric closure element and which is capped by the outer cap, the latter including (means) a radially extending flange by which it maybe forced rearwardly relative to the inner cap so that the inwardly facing piercing needle of the outer cap penetrates the inner cap;
   (c) a generally cylindrical vial closed at its front end by said elastomeric closure element and open at its rear end, the vial when stood on its rear end being stable against tipping and any external flange at the rear end being too small to cause substantial tipping of the vial when conveyed in a vertical attitude adjacent other similar vials through filling and capping equipment;
   (d) a substantially solid elastomeric piston axially movable within the vial and maintaining a first component of a syringe dispensable preparation sealed within said vial between the inner cap and the piston, the piston having a rearward extension within the vial, a comparatively narrow axial passage defined therethrough, and an integral needle penetrable resilient septum closing said passage;
   (e) a hollow cylindrical syringe actuating plunger to the rear of the piston, the rearward extension of the piston and the front end of the plunger having coupling means enabling the plunger to be manipulated from a rearward position relative to the piston to a forward position relative to the piston;
   (f) a third cap received within and releasably engageable with the interior of the front end of the plunger, the third cap having a double ended hollow needle having both forward and rearward projections, the forward projection of the needle being such that when the cap is engaged with the plunger, and the plunger is in its rearward position relative to the piston, the needle does not penetrate the septum of the piston and when the plunger is in its forward position relative to the piston the needle does penetrate the septum of the piston; and
   (g) a sealed collapsible capsule containing a second, liquid component of the preparation, the capsule having a front portion entering the rear end of the plunger and engaging the third cap, and a deformable rear portion extending rearwardly of the plunger whereby the rear portion may be manipulated to drive the forward portion of the capsule onto the rearward projection of the needle and permit the contents of the capsule to be discharged through the needle.

2. A vial formed of rigid transparent material and consisting of a cylindrical body, said body having an open bottom end having an external diameter at most only slightly greater than that of the remainder of the body, but sufficient to support the body in a stable manner when conveyed standing on its open end through vial filling and capping machinery, injectable material within the body, a comparatively wide neck at the top of the body through which said injectable material is filled into the body, an external peripheral flange surrounding the neck, an elestomeric closure applied to the neck, a cylindrical cap clamped onto the flange of the neck and having an annular inward extending flange at a top end overlying the closure to secure the closure to the neck with the closure presenting a needle penetrable central portion, an impervious piston of resilient material sealingly received within said body beneath said injectable material and above said bottom end, and coupling means connectable to a syringe plunger and projecting downwardly from said piston but wholly within the body, whereby said vial maybe converted into a syringe for ejection of the injectable material on movement of the piston towards the neck, by connection of said syringe plunger to said coupling means and connection of fluid conduit coupling means to said cylindrical cap, wherein the piston is moulded from resilient material and defines relatively narrow axial passages extending to opposite sides of the piston, with a penetrable resilient septum between the passages.

3. A vial according to claim 4, wherein the coupling means for connection to the plunger is a screw threaded extension towards the open bottom end of the vial.

4. A syringe including a vial according to claim 2, a plunger connectable to said piston, and an outer cap engageable over the cap of said vial, the outer cap having a hollow needle projecting axially within the cap and a coupling for engagement with injection means and communicating with said hollow needle, the outer cap being axially movable relative to said cap of the vial from a position in which the needle ends short of the cap of the vial to a position in which it penetrates the elastomeric-closure of the vial.

5. A syringe according to claim 4, wherein both the plunger and the outer cap are provided with radially extending flanges providing opposed finger grips for operating the syringe.

6. A syringe including a vial according to claim 2, a tubular open ended plunger connectable to said piston, and an outer cap engageable over the cap of said vial, the outer cap having a hollow needle projecting axially within the cap and a coupling for engagement with injection means and communicating with said hollow needle, the outer cap being axially movable relative to said cap of the vial from a position in which the needle ends short of the elastomeric closure of the vial to a position in which it penetrates the cap of the vial.

7. A syringe according to claim 6, further including a capsule assembly comprising a generally cylindrical sealed capsule having walls formed of a flexible needle penetrable material, a generally cylindrical neck defined by said walls at one end of the capsule, said neck having axially spaced external peripheral ridges, and a generally cylindrical cap applied to said neck so that a detent within the cap engages a first of the peripheral ridges on the neck, a double ended hollow needle passing through said cap so that an inner end within the cap ends short of the neck of the capsule and an outer end extends outwardly of the cap, the cap being displaceable relative to the capsule to a position in which the detent rides over the other ridge and the inner end of the needle penetrates the neck of the capsule, the cap and capsule being of a diameter such that they can enter the tubular plunger to a position in which the outer end of the needle on the cap of the capsule penetrates the septum of the piston when the plunger is engaged with the latter.

8. A syringe according to claim 7, wherein the cap of the capsule has an external screw thread, and the tubular plunger has an internal screw thread engageable with said external thread.

9. A syringe according to claim 8, wherein the means on the piston for connection to the plunger is an external screw thread engageable with the internal screw thread of the tubular plunger.

10. A syringe including a vial according to claim 2, a plunger connected to the coupling means of said piston, and an outer cap engaged over the cap of said vial, both the plunger and the outer cap being provided with radially extending flanges, and the outer cap supporting hollow needle for movement means into a position in which an inner end of the needle means penetrates the elastomeric closure of the vial.

11. A syringe including a vial according to claim 2, a plunger connector to the coupling means of said piston, and an outer cap engaged over the cap of said vial, both the plunger and the outer cap being provided with radially extending flanges, and the outer cap supporting hollow needle means for movement into a position in which an inner end of the needle means penetrate the elastomeric closure of the vial.

12. A syringe according to claim 14, further including a capsule assembly comprising a generally cylindrical sealed capsule having walls formed of a flexible needle penetrable material, a generally cylindrical neck defined by said walls at one end of the capsule, said neck having axially spaced peripheral ridges, and a generally cylindrical cap applied to said neck so that a detent within the cap engages one of the peripheral ridges on the neck, a double ended hollow needle passing through said cap so that an inner end within the cap ends short of the neck of the capsule and an outer end extends outwardly of the cap, the cap having being displaceable relative to the capsule to a position in which the detent rides over the other ridge and the inner end of the needle penetrates the neck of the capsule, the cap and capsule being of a diameter such that they can enter the tubular plunger to a position in which the outer end of the needle on the cap of the capsule penetrates the septum of the piston when the plunger is engaged with the latter, and the cap having means on its external peripheral surface for releasable engagement with the plunger at its internal peripheral surface.

13. A capsule assembly containing a liquid for delivery though a needle, comprising a generally cylindrical sealed capsule having walls formed of a flexible needle penetrable material, a generally cylindrical neck defined by said walls at one end of the capsule, said neck having axially spaced external peripheral ridges, and a generally cylindrical cap applied to said neck so that a detent within the cap engages the one peripheral ridge on the neck, a double ended hollow needle passing through said cap so that an inner end within the cap ends short of the neck of the capsule and an outer end extends outwardly of the cap, the cap being displaceable relative to the capsule to a position in which the detent rides over the inner ridge and the inner end of the needle penetrates the neck of the capsule, and the cap has an external screw thread for engagement with a complimentary thread within a tubular plunger of a syringe, at least a portion of the capsule nearest the neck having a diameter small enough to enter said plunger.

* * * * *